Jan. 19, 1954 J. A. PODESTA Plant Pat. 1,243
ROSE PLANT
Filed Oct. 17, 1952
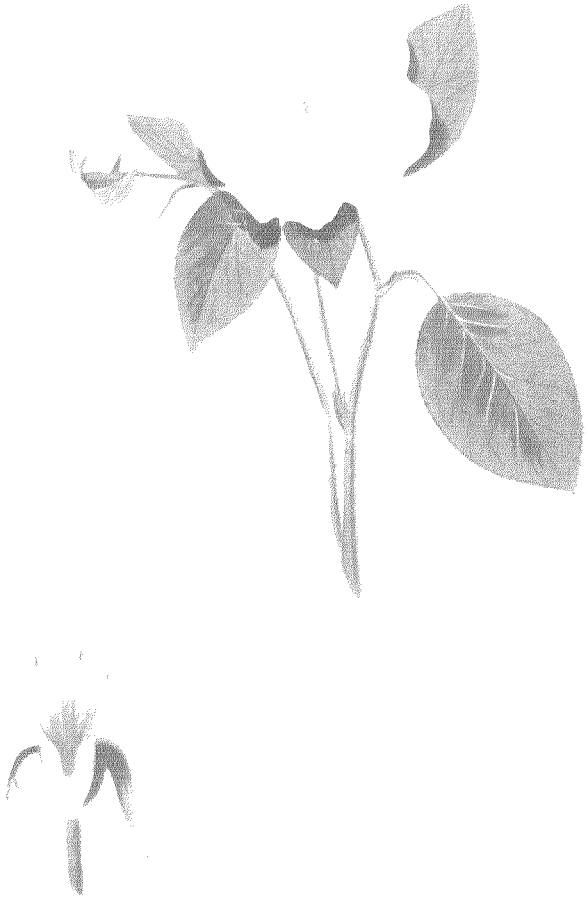
INVENTOR
John A. Podesta
By Orville M. Kile
Plant patent Agt.

Patented Jan. 19, 1954 Plant Pat. 1,243

UNITED STATES PATENT OFFICE 1,243

ROSE PLANT

John A. Podesta, San Leandro, Calif.

Application October 17, 1952, Serial No. 315,442

1 Claim. (Cl. 47—61)

My present discovery is an improved variety of polyantha rose plant, which originated as a cultivated sport of the variety Garnette (unpatented) and was discovered by me at San Leandro, California, in nurseries of which I am a part owner.

The new variety is much like its parent except for the color and structure of its flower and the tint and character of the foliage. It has been asexually reproduced by me from cuttings at the above-mentioned nurseries and its distinguishing characteristics appear to be permanently fixed.

The illustrations accompanying this specification are water color paintings of two specimens of the flower of this new variety in different stages of opening and in approximately their true coloring, together with an enlarged cross-section diagrammatic view of the tube-like center (receptacle) of one of the flowers, showing its peculiar typical formation.

In the following detailed description of the plant and flower, the plate numbers refer to Ridgway's Color Standards and Nomenclature.

*The plant*

Growth: Similar to that of its parent, Garnette, but not quite so bushy. Will grow to approximately 7 feet in height when untrimmed but in usual nursery practice is cut to 5½ or 6 feet.

Blooming habit: Continuous bloomer throughout the season.

Borne: Both singly and in clusters of 2 or 3, although there is greater tendency to single bloom than is the case with the parent plant.

Stems:

*Color.*—Between Lettuce Green and Spinach Green (Pl. V).

*Strength.*—Slender but strong.

*Thorns.*—None appear on the upper stem but some appear on the lower portion of the stem. These thorns are light green in color, large, sharp, downward-pointing and irregularly spaced.

Foliage:

*Type.*—Odd pinnately compound, with from 3 to 7 leaflets.

*Size.*—Terminal leaflet is approximately 2 inches long and 1⅜ inches wide as an average. Lateral leaflets progressively smaller, the first pair below the terminal leaflet being approximately 2 inches by 1 inch, while the second or last pair is about 1⅛ inches by ⅝ inch.

*Shape.*—Broadly oval, with rounded base and tip, with small sharp-pointed apex.

Margins finely serrated (finer serrations than in the case of the parent plant).

*Texture.*—Thin.

*Appearance.*—Lies flat with no undulations. Surface between the veins is slightly puffed and of a dull appearance.

*Color.*—Slightly lighter green than the foliage of the parent plant, being between Lettuce Green and Spinach Green (Pl. V).

*Rachis.*—Slender; deep-grooved on upper side. Usually smooth beneath.

*Stipules.*—Very small; almost lacking.

*The flower*

Bud:

*Borne.*—In stem axils.

*Size.*—Small. When color is showing just before unfurling, bud is approximately ¾ inch long.

*Shape.*—Blunt.

*Sepals.*—Small; mostly simple but some slightly branched.

*Opening.*—Even.

*Color.*—The half-opened bud is white with only occasional traces of green on the outer petals.

*Peduncle.*—Short; slender; strong; covered with tiny spines.

Bloom:

*Size.*—Small to medium, averaging 1½ to 2 inches in diameter.

*Form.*—Partly opened flower is loose with flat or depressed center. Opens flat with petals imbricated, the central petals very short and opened wide to show the green center.

*Center.*—The center of the flower is unique. The top of the receptacle forms a ring or collar from which the stamens grow, surrounded by the petals. There are only a very few stamens, and these are attached to the ring or collar. Filaments are greenish white and anthers yellows. Inside the ring no pistils are apparent but instead is a green growth with definite foliaceous formation, which arises above the ring as high or higher than the usual pistil. There are 15 to 20 "leaves" which make up the green center and these are distinctly separate. This structure results in a definite green center clearly visible in the fully opened flower.

*Color.*—The general color effect is pure white with green center visible when fully opened.

*Petalage.*—Averages about 40 petals, with 5 to 10 additional minute petaloids.

*Fragance.*—Little or none.

*Longevity.*—Lasts well, both on bush and as cut flower.

Petals:

*Size.*—Outer petals are approximately ⅞ inch by ¾ inch. Inner petals much smaller and shorter.

*Shape.*—Modified obovate, with inner petals narrower.

*Arrangement.*—Imbricated; slightly reflexed in fully-opened stage.

*Texture.*—Delicate and silky.

*Persistence.*—Petals cling well.

Having thus disclosed my discovery, I claim:

The new and distinct variety of polyantha type rose plant, substantially as herein described and illustrated, characterized particularly by its growth of medium height and bushiness; its relatively light-colored leaves with finely serrated edges; and its production throughout the season of white buds with little or no green on the petals, developing into completely double flowers having unique green centers with no pistils, as described.

JOHN A. PODESTA.

No references cited.